US00PP19566P2

(12) United States Plant Patent
Kristensen

(10) Patent No.: US PP19,566 P2
(45) Date of Patent: Dec. 9, 2008

(54) *OSTEOSPERMUM* PLANT NAMED 'SAKSISCOPYE'

(50) Latin Name: *Osteospermum hybrida*
Varietal Denomination: Saksiscopye

(75) Inventor: Niels G. Kristensen, Marslev (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 11/901,441

(22) Filed: Sep. 17, 2007

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
*Assistant Examiner*—June Hwu
(74) *Attorney, Agent, or Firm*—Jondle & Associates, P.C.

(57) ABSTRACT

A new *Osteospermum* plant particularly distinguished by having pale-yellow flowers with copper tips, medium flower size and compact plant growth habit, is disclosed.

1 Drawing Sheet

Genus and species: *Osteospermum hybrida.*
Variety denomination: 'Saksiscopye'.

BACKGROUND OF THE NEW PLANT

'Saksiscopye' originated from a hybridization of proprietary hybrid *Osteospermum* breeding line '203005' (unpatented) and commercial hybrid *Osteospermum* line 'Sunny Amanda' (U.S. Plant Pat. No. 16,522) in Aabyhoej, Denmark. The male parent, 'Sunny Amanda', has a pale-yellow flower color with terracotta-brown at the flower petal apices, medium flower size and brown disc florets. The female parent, '203005' has a bright-yellow flower color, medium flower size and a compact and less branching plant growth habit.

In spring 2003, the two *Osteospermum* lines were crossed and 552 seeds were obtained. The seeds were sown and 442 plants were grown in pots for evaluation. Out of 442 $F_1$ lines, plant number 206 was selected for its pale-yellow flowers with copper tips, medium flower size and a compact plant growth habit.

In spring 2004, plant number 206 was vegetatively propagated with cuttings and re-evaluated in an open field and a greenhouse. Plant number 206 was given the code number '204066'.

In spring 2005, plants were evaluated again in pots and in an open field. The selection '204066' was named 'Saksiscopye' and found to retain its distinctive characteristics through successive asexual propagations.

SUMMARY OF THE INVENTION

The following are the most outstanding and distinguishing characteristics of this new cultivar when grown under normal horticultural practices in Salinas, Calif.

1. Pale-yellow flower color with copper tips;
2. Medium flower size; and
3. Compact plant growth habit.

DESCRIPTION OF PHOTOGRAPH

This new *Osteospermum* plant is illustrated by the accompanying photograph which shows the plant's overall plant habit including form, foliage and flowers. The colors shown are as true as can be reasonably obtained by conventional photographic procedures.

DESCRIPTION OF THE NEW CULTIVAR

The following detailed descriptions set forth the distinctive characteristics of 'Saksiscopye'. The data which define these characteristics were collected from asexual reproductions carried out in Salinas, Calif. Data was collected on plants grown approximately six months from transplanting rooted cuttings into 5-inch pots under greenhouse conditions in Salinas, Calif. Color references are to the R.H.S. Colour Chart of The Royal Horticultural Society of London (R.H.S.), $4^{th}$ edition.

DESCRIPTION OF THE NEW PLANT

Classification:
*Family.*—Compositae.
*Botanical.*—*Osteospermum hybrida.*

Parentage:
*Female parent.*—An individual plant of *Osteospermum* line '203005' (unpatented).
*Male parent.*—An individual plant of *Osteospermum* line 'Sunny Amanda' (U.S. Plant Pat. No. 16,522).

Growth:
*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root-inducing solution in water. The trays are misted hourly during rooting.
*Environmental conditions for plant growth*—Rooted cuttings are transplanted to pots with a 16 cm diameter, one plant per pot. Peat-based growing media is used. The pots are watered using a 150–200 ppm fertilizer solution containing 18% nitrogen, 8% phosphorus and 18% potassium. The soil is allowed to dry between waterings. During the first few weeks after transplanting, the plants have evening temperatures around 15°–18° C. for good root growth. When plants reach 7.5–10 cm in height they are pinched back to 5–6 leaves to promote branching. Spring and summer daytime high temperatures in Salinas, Calif., where the data was collected, range from 16°–25° C.

*Time to bloom from propagation.*—Approximately four weeks after rooted vegetative cuttings are transferred to a 5-inch diameter pot. Flowering season is year-round in the United States. Vernalization is not required to induce flowering.

Plant description:

*Habit.*—Compact and branching.
*Life cycle.*—Perennial.
*Form.*—Branching, dense.
*Height (from soil line to first node).*—2 cm.
*Height (from soil line to top of foliage).*—18 cm to 20 cm.
*Width.*—23 cm to 25 cm.

Stems:

*Internode length.*—1.0 cm to 2.0 cm.
*Stem shape.*—Round.
*Stem diameter.*—0.4 cm to 0.5 cm.
*Stem color.*—RHS 187A (Greyed-purple) on 50% of the stem and RHS 1 38B (Green) on the other 50% of the stem; RHS 138B (green) at soil line.
*Pubescence.*—Heavy.
*Pubescence shape.*—Linear, fuzzy in appearance.
*Pubescence color.*—RHS N155A (White).
*Anthocyanin color.*—RHS 187A (Greyed-purple).

Leaves:

*Arrangement.*—Alternate.
*Shape.*—Oblanceolate.
*Apex.*—Acute.
*Base.*—Attenuate.
*Margin.*—Serrate.
*Venation.*—Anastomosing.
*Surface.*—Upper surface is smooth while lower surface is rough.
*Surface pubescence.*—Slight pubescence.
*Attachment.*—Decurrant.
*Length.*—3.5 cm to 4.0 cm.
*Width.*—1.5 cm.
*Thickness.*—0.5 cm.
*Color.*—Upper surface: RHS 138A (Green). Lower surface: RHS 138B (Green).
*Venation color (both surfaces).*—RHS 138B (Green).

Inflorescence:

*Number per plant.*—8.
*Type.*—Capitulum (head); Disc florets are perfect and ray florets are carpellate.
*Flowering habit.*—Determinate.
*Lastingness of flowers.*—3 to 4 days.
*Fragrance.*—None.
*Seed production.*—None observed.
*Diameter.*—7.0 cm.
*Depth.*—1.0 cm to 1.5 cm.
*Disc diameter.*—1.8 cm to 2.0 cm.
*Disc floret number.*—180 to 200 per inflorescence.
*Peduncle length.*—5.5 cm from inflorescence to first node.
*Peduncle diameter.*—0.25 cm.
*Peduncle color.*—RHS 138B (Green).
*Peduncle texture.*—Dull, moderate pubescent.
*Phyllaries.*—Arrangement: 22 per inflorescence, free, arranged symmetrically. Length: 1.0 cm to 1.2 cm. Width: 0.10 cm to 0.20 cm. Apex: Acute. Margin: Entire. Shape: Linear, acute. Color: Upper surface: RHS 138B (Green) with RHS 187A (greyed-purple) tips. Lower surface: RHS 138A (Green) with RHS 187A (greyed-purple) tips.

Ray florets (ligules):

*Corolla.*—One petal per ray floret; only the outer row of florets are the ray florets.
*Number of ray florets per inflorescence.*—26.
*Length.*—3.0 cm.
*Width.*—0.8 cm.
*Shape.*—Lanceolate.
*Apex.*—Acute.
*Margin.*—Entire.
*Color.*—Upper surface: RHS 12A (Yellow) with slight streaks of RHS 17A (Yellow-orange) and RHS 187A (Greyed-purple) at the tip. Lower surface: RHS 187A (Greyed-purple) with streaks of RHS 12A (Yellow) and RHS 187A (Greyed-purple) at the tip.
*Pubescence.*—Glabrous.
*Ovary.*—Superior.
*Pistil form.*—One style with two stigma branches.
*Pistil length.*—0.4 cm.
*Stigma color.*—RHS N187A (Greyed-purple).
*Style color.*—RHS N187A (Greyed-purple).

Disc florets:

*Color.*—RHS 133C (Green).
*Number.*—180 to 200 per inflorescence.
*Shape.*—Tubular.
*Apex.*—Rounded.
*Surface.*—Dull, pubescent.
*Size.*—Length: 0.5 cm. Width: 0.5 cm.
*Pistil form.*—One style with two stigma branches.
*Ovary.*—Superior.
*Style color.*—RHS N187A (Greyed-purple).
*Stigma color.*—RHS N187A (Greyed-purple).
*Stamens.*—5, fused into a single tube.
*Anther color.*—RHS N187A (Greyed-purple).
*Pollen color.*—RHS 17A (Yellow-orange).
*Filament color.*—RHS 11A (Yellow).

Disease and insect resistance: Very disease resistant, however, plants are susceptible to aphids, thrips, whiteflies and worms.

COMPARISON WITH PARENTAL LINES AND KNOWN CULTIVARS

'Saksiscopye' is a distinct variety of *Osteospermum* owing to its pale-yellow flower color with copper tips, medium flower size and compact plant growth habit. 'Saksiscopye' is distinguished from its parents primarily by ray floret color, flower size, disc floret color and plant growth habit as described in Table 1 (color references are to The Royal Horticultural Society Colour Chart, $4^{th}$ edition):

TABLE 1

Comparison with Parental Lines

| Characteristic | 'Saksiscopye' | Male Parent 'Sunny Amanda' (U.S. Plant Patent No. 16,522) | Female Parent '203005' |
|---|---|---|---|
| Ray floret (ligule) color, upper surface: | RHS 12A (Yellow) with slight streaks of RHS 17A (yellow-orange) and RHS 187A (greyed-purple) at the tip | Pale yellow with terracotta-brown tips | Bright yellow |
| Flower size | Large | Medium | Medium |
| Disc florets color | Green | Blue | Green-Brown |
| Plant habit | Mounded and compact | Globular | Compact |

'Saksiscopye' is most similar to the *Osteospermum* plant 'Summertime Sunrise' (unpatented); however, there are differences as described in Table 2 (color references are to The Royal Horticultural Society Colour Chart, 4$^{th}$ edition):

TABLE 2

Comparison with Similar Variety

| Characteristic | 'Saksiscopye' | 'Summertime Sunrise' |
|---|---|---|
| Ray floret (ligule) color, upper surface: | RHS 12A (Yellow) with slight streaks of RHS 17A (yellow-orange) and RHS 187A (greyed-purple) at the tip | Pale yellow-cream with pink streaks and a pink ring around flower eye |
| Ray floret (ligule) color, lower surface: | RHS 187A (Greyed-purple) streaks of RHS 12A (yellow) streaks and RHS 187A (greyed-purple) at the tip | Yellow with grey-brown stripes |
| Plant growth habit | Very compact | Compact |
| Flower stalk length | Short | Medium |

I claim:

1. A new and distinct cultivar of *Osteospermum* plant as shown and described herein.

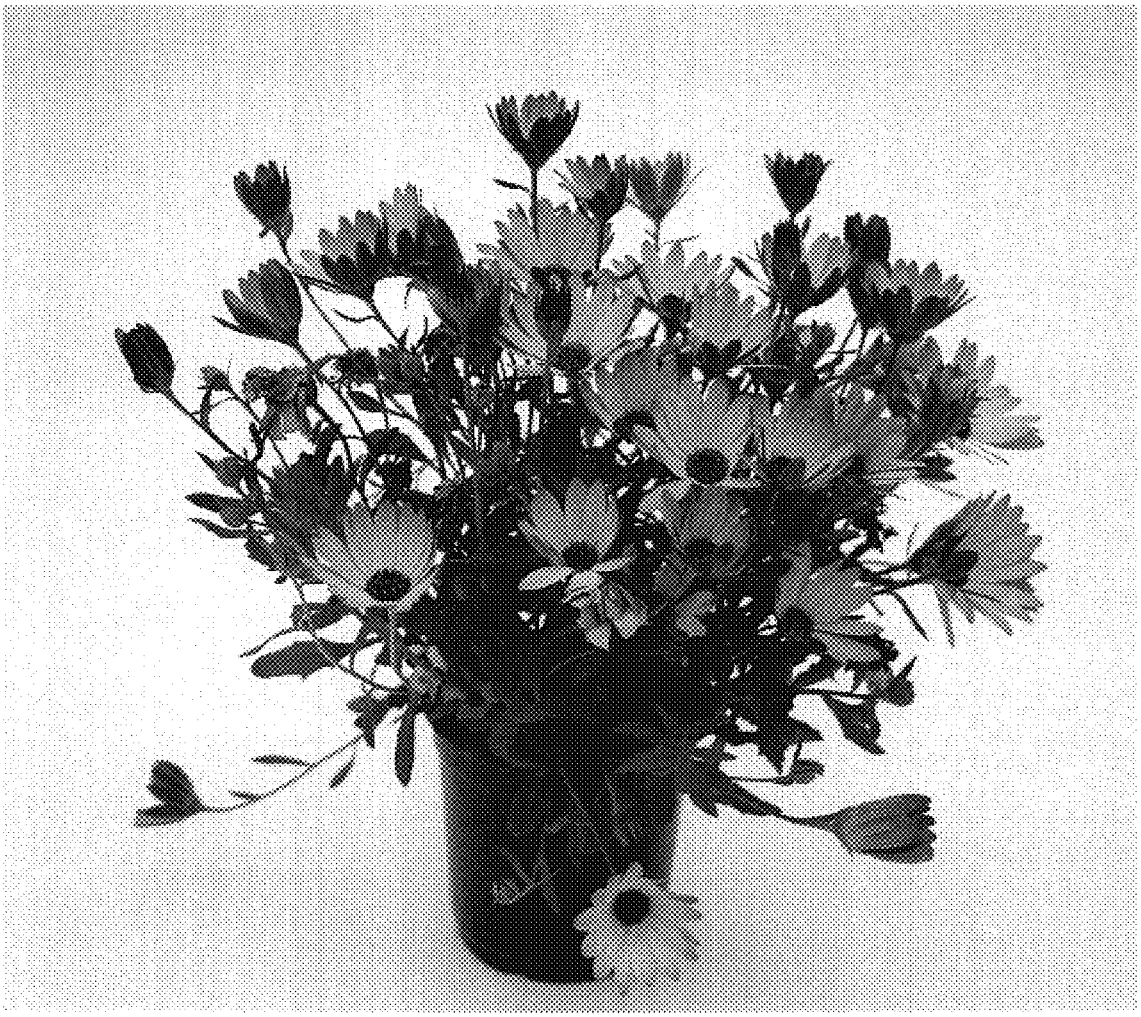

* * * * *